United States Patent [19]
Reinhartz et al.

[11] Patent Number: 5,527,673
[45] Date of Patent: Jun. 18, 1996

[54] APPARATUS AND METHOD FOR TRANSPORT OF NUCLEIC ACID SEQUENCES BY CAPILLARY ACTION ON A SOLID SUPPORT AND DETECTION OF THE NUCLEIC ACID SEQUENCES

[75] Inventors: Avraham Reinhartz, Rehovot; Sarah Alajem, Kfar Hanagid, both of Israel; Thierry Paper, Paris, France; Max Herzberg, Satariya, Israel

[73] Assignee: Orgenics Ltd., Yavne, Israel

[21] Appl. No.: 306,254

[22] Filed: Sep. 14, 1994

Related U.S. Application Data

[63] Continuation of Ser. No. 952,573, Sep. 28, 1992, abandoned.

[30] Foreign Application Priority Data

Oct. 4, 1991 [IL] Israel .......................................... 99647
Jul. 13, 1992 [IL] Israel ........................................ 102486

[51] Int. Cl.[6] .............................. C12Q 1/68; C12P 19/34; G01N 21/01
[52] U.S. Cl. ............................... 435/6; 435/91.2; 436/94; 436/807; 422/56; 422/58; 422/68.1; 422/69; 422/70; 536/25.4
[58] Field of Search ...................... 435/6, 91.2; 436/807, 436/808, 809, 810, 94; 422/56, 58, 68.1, 69, 70; 536/25.4

[56] References Cited

U.S. PATENT DOCUMENTS

| | | | |
|---|---|---|---|
| 4,652,517 | 3/1987 | Scholl | 435/5 |
| 4,822,731 | 4/1989 | Watson | 435/6 |
| 4,931,223 | 6/1990 | Bronstein | 252/700 |
| 4,956,275 | 9/1990 | Zuk | 435/7 |
| 4,963,658 | 10/1990 | Kung et al. | 530/406 |
| 5,194,370 | 3/1993 | Berninger et al. | 435/6 |
| 5,262,299 | 11/1993 | Evangelista et al. | 435/6 |

FOREIGN PATENT DOCUMENTS

| | | |
|---|---|---|
| 0262328 | 4/1988 | European Pat. Off. . |
| 0306336 | 3/1989 | European Pat. Off. . |
| 0318255 | 5/1989 | European Pat. Off. . |
| 0362809 | 4/1990 | European Pat. Off. . |
| 2191577 | 12/1987 | United Kingdom . |
| 89/10979 | 11/1989 | WIPO . |
| 91/06659 | 5/1991 | WIPO . |

OTHER PUBLICATIONS

Sauvaigo et al., *Nucleic Acids Res.* 18(11), 3175–3183 (1990).

*Primary Examiner*—Kenneth R. Horlick
*Attorney, Agent, or Firm*—Ladas & Parry

[57] ABSTRACT

Apparatus for transport of molecules including nucleic acid sequences in a bibulous carrier comprising a dry bibulous carrier defining a capillary transport path which supports the transport of the molecules when contacted with a solution containing the molecules.

7 Claims, 2 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 25
        ( B ) TYPE: Nucleotide
        ( C ) STRANDEDNESS: Single
        ( D ) TOPOLOGY: Linear     ( x i ) SEQUENCE DESCRIPTION: SEQ ID NO:1:

TGGGAAGTTC AATTAGGAAT ACCAC 25

( 2 ) INFORMATION FOR SEQ ID NO:2:

( i ) SEQUENCE CHARACTERISTICS:
        ( A ) LENGTH: 21
        ( B ) TYPE: Nucleotide
        ( C ) STRANDEDNESS: Single
        ( D ) TOPOLOGY: Linear     ( x i ) SEQUENCE DESCRIPTION: SEQ ID NO:2:

TGGGAAGTTC AATTAGGAAT A 21

( 2 ) INFORMATION FOR SEQ ID NO:3:

( i ) SEQUENCE CHARACTERISTICS:
        ( A ) LENGTH: 26
        ( B ) TYPE: Nucleotide
        ( C ) STRANDEDNESS: Single
        ( D ) TOPOLOGY: Linear     ( x i ) SEQUENCE DESCRIPTION: SEQ ID NO:3:

CCTACATACA AATCATCCAT GTATTC 26

( 2 ) INFORMATION FOR SEQ ID NO:4:

( i ) SEQUENCE CHARACTERISTICS:
        ( A ) LENGTH: 21
        ( B ) TYPE: Nucleotide
        ( C ) STRANDEDNESS: Double
        ( D ) TOPOLOGY: Linear     ( x i ) SEQUENCE DESCRIPTION: SEQ ID NO:4:

AAGGGAGTAA CCGAAATCGG T 21

( 2 ) INFORMATION FOR SEQ ID NO:5:

( i ) SEQUENCE CHARACTERISTICS:
        ( A ) LENGTH: 22
        ( B ) TYPE: Nucleotide
        ( C ) STRANDEDNESS: Double -continued (D) TOPOLOGY: Linear (xi) SEQUENCE DESCRIPTION: SEQ ID NO:5:

ATAATGTCTA TATTCACTAA TT                                                22

(2) INFORMATION FOR SEQ ID NO:6:

(i) SEQUENCE CHARACTERISTICS:
(A) LENGTH: 20
(B) TYPE: Nucleotide
(C) STRANDEDNESS: Single
(D) TOPOLOGY: Linear (xi) SEQUENCE DESCRIPTION: SEQ ID NO:6:

TATTCCTAAT TGAACTTCAA                                                   20

(2) INFORMATION FOR SEQ ID NO:7:

(i) SEQUENCE CHARACTERISTICS:
(A) LENGTH: 21
(B) TYPE: Nucleotide
(C) STRANDEDNESS: Double
(D) TOPOLOGY: Linear (xi) SEQUENCE DESCRIPTION: SEQ ID NO:7:

AAGGGCGTAA CCGAAATCGG T                                                 21

(2) INFORMATION FOR SEQ ID NO:8:

(i) SEQUENCE CHARACTERISTICS:
(A) LENGTH: 19
(B) TYPE: Nucleotide
(C) STRANDEDNESS: Double
(D) TOPOLOGY: Linear (xi) SEQUENCE DESCRIPTION: SEQ ID NO:8:

GTTGTTTGCA GCTCTGTGC                                                    19

(2) INFORMATION FOR SEQ ID NO:9:

(i) SEQUENCE CHARACTERISTICS:
(A) LENGTH: 37
(B) TYPE: Nucleotide
(C) STRANDEDNESS: Double
(D) TOPOLOGY: Linear (xi) SEQUENCE DESCRIPTION: SEQ ID NO:9:

CAACAACAAC AAGTTTCAGG ACCCACAGGA GCGACCC                                 37

APPARATUS AND METHOD FOR TRANSPORT OF NUCLEIC ACID SEQUENCES BY CAPILLARY ACTION ON A SOLID SUPPORT AND DETECTION OF THE NUCLEIC ACID SEQUENCES

This is a continuation of application Ser. No. 07/952,573 filed on Sep. 28, 1992, abandoned

FIELD OF THE INVENTION

The invention relates to apparatus and methods for separation of target molecules including target nucleic acid sequences from oligonucleotides, and nucleotides and concentration and detection of the molecules.

BACKGROUND OF THE INVENTION

The use of amplification techniques in a procedure for detection of a target molecules that include target nucleic acid sequences is well known in the art. Typically, this procedure includes enzymatic amplification of target nucleic acid sequences and detection of the target molecules by gel electrophoresis followed by Southern blot procedures.

A number of solid phase capture assays have also been developed to simplify the procedures for detection of target molecules including nucleic acid sequences. In these procedures two ligands are typically incorporated within amplified target nucleic acid sequences. A first ligand is used to capture, on a solid matrix, the target molecules that include the amplified target nucleic acid sequences and a second ligand is used to detect the target molecules by the binding of a signal producing reagent to this second ligand.

Solid phase affinity capture assays, however, require an extended reaction time to capture a high proportion of target molecules in a reaction mixture (Sauvaigo et al., Nucleic Acid Research, 1990, Vol. 18, pp. 3175–3182). Furthermore, when capture is mediated by amplification primers incorporating a solid phase affinity ligand, the sensitivity of the assay may be adversely effected by competition between free primers and primers incorporated in the target nucleic acid sequences.

The use of chromatography as a separation and concentration procedure is well known in the art. It has been reported that whereas DNA molecules are chromatographically mobile on moistened paper they fail to migrate when solutions are applied to dry paper (Bendich et al., Arch. Biochem. Biophys., 1961, 94, 417–423).

SUMMARY OF THE INVENTION

One object of the present invention is to provide a method and apparatus for capillary transport of molecules including nucleic acid sequences.

Another object of the present invention is to provide a method and apparatus for concentration of target molecules including target nucleic acid sequences in a liquid sample.

A further object of the present invention is to provide a method and apparatus for the separation of target molecules including target nucleic acid sequences from nucleotides and oligonucleotides.

Another object to the present invention is to provide a method for the detection of target molecules including specific nucleic acid sequences.

There is thus provided in accordance with the present invention apparatus for transport of molecules including nucleic acid sequences in a bibulous carrier comprising a dry bibulous carrier defining a capillary transport path which supports the transport of the molecules when contacted with a solution containing the molecules.

In accordance with a preferred embodiment of the invention apparatus for concentration of target molecules in a liquid sample is provided including the dry bibulous carrier wherein the target molecules include target nucleic acid sequences and are transported within the bibulous carrier by capillary action when a portion of the dry bibulous carrier contacts the liquid sample containing the target molecules, and at least one capture reagent immobilized in at least one capture zone on the dry bibulous carrier downstream of a contact portion of the bibulous carrier wherein the at least one capture reagent is capable of capturing the target molecules.

There is also provided in accordance with the present invention apparatus for separation of target molecules, including target nucleic acid sequences, from non-target nucleotides and oligonucleotides in a liquid sample containing the target molecules and the non-target nucleotides and oligonucleotides comprising, a vessel containing a compound that binds the non-target oligonucleotides, and apparatus for transporting the target molecules from the vessel by capillary action.

In accordance with a preferred embodiment of the invention the dry bibulous carrier is a nitrocellulose membrane wherein the absorption sites have been blocked to facilitate capillary transport of the target molecules.

In accordance with another preferred embodiment of the invention the dry bibulous carrier is supported by a rigid frame.

In accordance with still another preferred embodiment of the invention an absorbent pad is fixed to the dry bibulous carrier downstream from the at least one capture zone to facilitate capillary transport of a liquid through the dry bibulous carrier.

In accordance with yet another a preferred embodiment of the invention the absorption sites of the nitrocellulose membrane are blocked by compounds selected from a group comprising macromolecules, detergents and combinations thereof.

In accordance with still another preferred embodiment of the invention the macromolecules include proteins.

In accordance with still a further preferred embodiment of the invention the at least one capture reagent includes an antibody to a modified portion of the target nucleic acid sequences.

In accordance with another preferred embodiment of the invention the at least one capture reagent includes at least one nucleic acid capture reagent including nucleic acid probe sequences complementary to at least part of the target nucleic acid sequences.

In accordance with still another preferred embodiment of the invention the nucleic acid probe sequences include DNA sequences.

In accordance with yet another preferred embodiment of the invention the nucleic acid probe sequences include RNA sequences.

In accordance with a further preferred embodiment of the invention the target molecules include target nucleic acid sequences comprising more that 30 base pairs.

In accordance with another preferred embodiment of the invention wherein the target molecules including nucleic acid sequences include a nucleic acid product of an enzymatic amplification reaction and incorporate at least one pair of oligonucleotide primers.

In accordance with still another preferred embodiment of the invention the at least one pair of primers include primers for a polymerase chain reaction (PCR).

In accordance with a further preferred embodiment of the invention the at least one pair of primers include primers for a ligase chain reaction (LCR).

In accordance with yet a further preferred embodiment of the invention at least a second primer of the at least one pair of primers includes an oligonucleotide bearing a ligand which binds to at least one capture reagent whereby the target molecules which include the at least one primer bearing the ligand may be bound to the at least one capture reagent.

In accordance with still a further preferred embodiment of the invention the ligand which binds to at the least one capture reagent includes an antigenic epitope.

In accordance with another preferred embodiment of the invention the ligand which binds to the at least one capture reagent includes at least one sulfonated cytosine.

In accordance with yet another preferred embodiment of the invention the compound includes gel filtration particles too large to be transported by the apparatus for transporting.

In accordance with a yet another preferred embodiment of the invention the non-target oligonucleotides include oligonucleotide primers not incorporated in the target nucleic acid sequences.

In accordance with a further preferred embodiment of the invention the compound includes a matrix unable to be transported by the means for transporting and wherein the compound hybridizes to the non-target oligonucleotide.

There is also provided in accordance with the present invention a method for transport of molecules including nucleic acid sequences in a bibulous carrier including the steps of, providing a dry bibulous carrier defining a capillary transport path which supports the transport of molecules including nucleic acid sequences, and contacting the dry bibulous carrier with a solution containing molecules including nucleic acid sequences.

There is additionally provided in accordance with the present invention a method for concentration of molecules, including nucleic acid sequences, in a liquid sample including the steps of, providing a dry bibulous carrier wherein the molecules are target molecules including target nucleic acid sequences and wherein the molecules are transported within the bibulous carrier by capillary action when a portion of the dry bibulous carrier contacts the liquid sample containing the molecules, contacting a portion of the dry bibulous carrier with the liquid sample containing the target molecules wherein the dry bibulous carrier, when wet, defines a liquid transport path which supports the transport of molecules including nucleic acid sequences, transporting the target molecules along the liquid transport path, and capturing the target molecules with at least one capture reagent immobilized in at least one capture zone on the dry bibulous carrier downstream of the portion of bibulous carrier contacting the liquid sample.

There is further provided according to the present invention a method for separation of target molecules, including target nucleic acid sequences, from non-target nucleotides and oligonucleotides, in a liquid sample containing the target molecules and the non-target nucleotides and oligonucleotides including the steps of, providing a vessel containing a compound that binds the non-target nucleotide and oligonucleotide sequences, adding the liquid sample which includes the target molecules and the non-target nucleotide and oligonucleotides, and transporting the target molecules by capillary action.

There is also provided in accordance with the present invention apparatus for separation of target molecules, including target nucleic acid sequences, from non-target nucleotides and oligonucleotides in a liquid sample containing the target molecules and the non-target nucleotides and oligonucleotides, concentration of the target molecules, and detection of the concentrated target molecules including, a vessel apparatus defining a plurality of wells including a first portion of the plurality of wells containing a compound that binds the non-target oligonucleotides and wherein the liquid sample may be added to the first portion of the plurality of wells, a dry bibulous carrier defining a liquid transport path from the vessel, that, when wet, supports the transport of the target molecules, wherein the target molecules are transported within the bibulous carrier by capillary action when a contact portion of the dry bibulous carrier contacts the liquid sample containing the target molecules, at least one capture reagent capable of capturing the target molecules wherein the at least one capture reagent is immobilized in at least one capture zone on the dry bibulous carrier downstream of the contact portion of the bibulous carrier, and apparatus for detecting the captured target molecules.

There is further provided in accordance with the present invention a method for concentration and detection of target nucleic acid sequences, in a liquid sample including the steps of, providing a dry bibulous carrier wherein the target nucleic acid sequences are transported within the bibulous carrier by capillary action when a portion of the dry bibulous carrier contacts the liquid sample containing the target nucleic acid sequences, contacting a portion of the dry bibulous carrier with the liquid sample containing the target nucleic acid sequences wherein the dry bibulous carrier, when wet, defines a liquid transport path which supports the transport of the target nucleic acid sequences, transporting the target nucleic acid sequences along the liquid transport path and capturing the target nucleic acid sequences by hybridization with at least one nucleic acid capture reagent immobilized in at least one capture zone on the dry bibulous carrier downstream of the portion of bibulous carrier contacting the liquid sample. There is still further provided in accordance with the present invention apparatus for concentration and detection of target nucleic acid sequences including, a vessel apparatus defining a plurality of wells, a dry bibulous carrier defining a liquid transport path from the vessel that when wet supports the transport of the target nucleic acid sequences wherein the target nucleic acid sequences are transported within the bibulous carrier by capillary action when a contact portion of the dry bibulous carrier contacts the liquid sample containing the target nucleic acid sequences, at least one nucleic acid capture reagent including nucleic acid probe sequences for capturing the target nucleic acid sequences by hybridization and wherein the at least one nucleic acid capture reagent is immobilized in a capture zone on the dry bibulous carrier downstream of the contact portion of the bibulous carrier, and apparatus for detecting the captured the target nucleic acid sequences.

In accordance with a preferred embodiment of the invention the apparatus for detecting includes a bibulous carrier upon which target molecules bearing a ligand which binds to a signal producing reagent are immobilized, and apparatus for contacting the target molecules bearing the ligand with the signal producing reagent to produce a sensible signal indicating the detection of the target molecules.

In accordance with a further preferred embodiment of the invention the apparatus for detecting includes a bibulous carrier upon which target molecules bearing a ligand which binds to a signal producing reagent are immobilized, and apparatus for contacting the target molecules bearing the ligand with the signal producing reagent which react with a color developing reagent to produce a sensible signal indicating the detection of the target molecules.

In accordance with another preferred embodiment of the invention the target nucleic acid sequences are the product of an enzymatic amplification reaction and incorporate at least one pair of oligonucleotide primers.

In accordance with yet another preferred embodiment of the invention the non-target oligonucleotides include oligonucleotide primers not incorporated in the target nucleic acid sequences.

In accordance with still another preferred embodiment of the invention the at least two sets of primers include primers for a polymerase chain reaction (PCR).

In accordance with a further preferred embodiment of the invention the at least one pair of primers include primers for a ligase chain reaction (LCR).

In accordance with still a further preferred embodiment of the invention a second primer of the at least one pair of oligonucleotide primers includes a ligand which binds to the at least one capture reagent whereby the target molecules that include the ligand may be bound to the at least one capture reagent.

In accordance with yet a further preferred embodiment of the invention the ligand which binds to the at least one capture reagent includes an antigenic epitope.

In accordance with another preferred embodiment of the invention the ligand which binds to the at least one capture reagent includes at least one sulfonated cytosine.

In accordance with still another preferred embodiment of the invention a first primer of the at least one pair of primers includes a ligand which binds to a signal producing reagent whereby the target molecules that include the ligand may be detected by the presence of a signal produced by the signal producing reagent.

In accordance with a further preferred embodiment of the invention the first primer of the at least one pair of primers includes a ligand which binds to a signal producing reagent whereby the target molecules that include the ligand may be detected by the presence of a signal produced by the signal producing reagent after contacting a signal developing reagent.

In accordance with yet another preferred embodiment of the invention the ligand which binds to the signal producing reagent includes biotinylated nucleotide sequences. In accordance with a further preferred embodiment of the invention the signal producing reagent includes streptavidin linked to colored latex beads.

In accordance with another preferred embodiment of the invention the signal produced by the signal producing reagent after contacting the signal developing reagent includes a streptavadin-alkaline phosphatase conjugate.

In accordance with another preferred embodiment of the invention the first portion of wells also contains the signal producing reagent.

In accordance with yet a further preferred embodiment of the invention the plurality of wells additionally includes a second portion of the wells containing a washing solution.

In accordance with still another preferred embodiment of the invention the plurality of wells also includes a third portion of the wells containing a signal developing reagent solution.

In accordance with yet another preferred embodiment of the invention the dry bibulous carrier includes at least one strip.

In accordance with a further preferred embodiment of the invention the plurality of wells include a first portion of wells containing a sample to be tested for the target nucleic acid sequences.

In accordance with another preferred embodiment of the invention the plurality of wells additionally include a second portion of the wells containing the signal producing reagent.

In accordance with yet another preferred embodiment of the invention the plurality of wells additionally includes a third portion of wells containing a washing solution.

In accordance with still another preferred embodiment of the invention the plurality of wells additionally includes a fourth portion of wells containing a signal developing reagent.

In accordance with a further preferred embodiment of the invention each of the first portion of wells are adapted to receive the contact portion of each strip to permit transport of the target molecules to the at least one capture zone where they are captured.

In accordance with still a further preferred embodiment of the invention each of the second portion of wells are adapted to receive the contact portion of each strip for washing the strip to remove non-specifically captured compounds after immobilization of the target molecules in the at least one capture zone.

In accordance with yet a further preferred embodiment of the invention each of the third portion of wells is adapted to receive an entire strip.

In accordance with another preferred embodiment of the invention the apparatus for contacting includes, at least one of the third portion of wells containing a signal producing reagent solution, and at least one strip after immobilization of the target nucleic acid in the at least one capture zone wherein the entire strip is in contact with a signal developing reagent solution permitting contact of the signal developing reagent with the at least one capture zone.

In accordance with yet another preferred embodiment of the invention each of the first portion of wells is adapted to receive the contact portion of each strip to permit transport of the target nucleic acid sequences to the at least one capture zone where they are captured.

In accordance with still another preferred embodiment of the invention each of the second portion of wells is adapted to receive the contact portion of each strip to permit transport of the signal producing reagent to the at least one capture zone where the signal producing reagent is bound to the ligand borne on the target nucleic acid sequences.

In accordance with a further preferred embodiment of the invention each of the third portion of wells is adapted to receive the contact portion of each strip for washing the strip to remove non-specifically captured compounds after immobilization of the target nucleic acid sequences in the at least one capture zone.

In accordance with yet a further preferred embodiment of the invention the apparatus for contacting includes, at least one of the fourth portion of wells containing a signal developing reagent, and at least one strip after immobilization of the target nucleic acid sequences in the at least one capture zone wherein the entire strip is in contact with the signal developing reagent solution per,hitting contact of the signal developing reagent with the at least one capture zone.

In accordance with a still further preferred embodiment of the invention each of the fourth portion of wells is adapted to receive an entire strip.

There is also provided in accordance with the present invention a method for the detection of a specific nucleic acid sequence including the steps of, amplifying by an enzymatic reaction at least a portion of an original nucleic acid sequence to produce target molecules including nucleic acid sequences which are specific to the at least a portion of the original nucleic acid sequence, separating the target molecules from non-target nucleotides and oligonucleotides including the steps of, providing a vessel containing a substrate that binds the non-target nucleotides and oligonucleotides, adding a liquid sample which includes the target molecules and the non-target nucleotides and oligonucleotides, and transporting the target molecules by capillary action, concentrating the target molecules including the steps of, providing a dry bibulous carrier wherein the target molecules are transported within the bibulous carrier by capillary action when a portion of the dry bibulous carrier contacts the liquid sample containing the target molecules, contacting a portion of the dry bibulous carrier with the liquid sample containing the target nucleic acid sequences wherein the dry bibulous carrier, when wet, defines a liquid transport path which supports the transport of the target molecules transporting the target molecules along the liquid transport path and capturing the target molecules with at least one capture reagent immobilized in at least one capture zone on the dry bibulous carrier downstream of the portion of bibulous carrier contacting the liquid sample, and detecting the target molecules by contacting target molecules having a ligand which binds to a signal producing reagent and are immobilized on a bibulous carrier with a signal producing reagent to produce a sensible signal.

There is also provided in accordance with the present invention a method for the detection of a specific nucleic acid sequence comprising the steps of, amplifying by an enzymatic reaction at least a portion of an original nucleic acid sequence to produce target nucleic acid sequences which are specific to the at least a portion of the original nucleic acid sequence, providing a liquid sample which includes the target nucleic acid sequences, transporting the target nucleic acid sequences by capillary action, concentrating the target nucleic acid sequences including the steps of providing a dry bibulous carrier wherein the target nucleic acid sequences are transported within the bibulous carrier by capillary action when a portion of the dry bibulous carrier contacts the liquid sample containing the target nucleic acid sequences, contacting a portion of the dry bibulous carrier with the liquid sample containing the target nucleic acid sequences wherein the dry bibulous carrier, when wet, defines a liquid transport path which supports the transport of the target nucleic acid sequences, and transporting the target nucleic acid sequences along the liquid transport path, capturing the target nucleic acid sequences with at least one nucleic acid capture reagent immobilized in at least one capture zone on the dry bibulous carrier downstream of the portion of bibulous carrier contacting the liquid sample and detecting the target nucleic acid sequences by contacting target nucleic acid sequences having a ligand which binds to a signal producing reagent and are immobilized on a bibulous carrier with a signal developing reagent to produce a sensible signal.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENTS

Reference is now made to FIGS. 1–4 which illustrates apparatus 10 for separation of a target molecules including target nucleic acid sequences from non-target nucleotides and oligonucleotides in a liquid sample, concentration of the target molecules, and detection of the concentrated target molecules constructed and operative in accordance with a preferred embodiment of the present invention.

Apparatus 10 includes vessel apparatus 12 fabricated from a non-porous material such as polystyrene and including one or more of a plurality of wells such as wells 14, 16 and 18. The wells, such as wells 14, 16, and 18, are approximately 1 cm in length, 0.5 cm in width, and 2.5 cm in depth, and are sized to receive the a contact portion 20 of a strip 22.

The strip 22 includes a bibulous carrier 24 typically embodied in a mylered nitrocellulose membrane approximately 3.0 cm in length and 0.5 cm in width and having a pore size of 3–5 microns which may be surrounded by a support frame 26. The support frame 26 is fabricated from a non-porous material such as polystyrene, and bibulous carrier 24 may be mounted in frame 22 by any convenient means such as gluing. An absorbent pad 27 approximately 2 cm in length and 0.5 cm in width, fabricated from an absorbent material such as Whatman 3MM paper (commercially available from Whatman, Maidstone, U.K.) is attached to the end of the strip 22 opposite the contact portion 20 by any convenient means such as gluing. The end of strip 22 is also attached to a handle 28 by any convenient means such as gluing. The handle 28 is fabricated from a non-porous material such as polystyrene. At least one strip 22 is attached to the handle 28 to form a test member 30.

A single capture reagent is typically immobilized on the bibulous carrier 24 in the central area of the bibulous carrier, to form a capture zone 32. Although a single capture reagent is typically employed, multiple capture reagents may be used to form multiple capture zones on a single bibulous carrier.

The single capture reagent, typically an anti-sulfonated DNA antibody or a nucleic acid complementary to at least part of the target nucleic acid sequence, is typically immobilized by absorption on the nitrocellulose membrane.

Wells 14 typically contain an enzymatic amplification reaction mixture. In addition, when the capture reagent is an anti-sulfonated DNA antibody the wells 14 also typically contain gel filtration particles (not shown), typically Sephadex G-100 (Pharmacia, Uppsala, Sweden) gel filtration particles. The gel filtration particles are sized to be too large to be transported by capillary action in the bibulous carrier 24.

The procedure used to detect specific nucleic acid sequences using apparatus 10 typically includes the enzymatic amplification of the specific nucleic acid sequence using Polymerase Chain Reaction (PCR) or Ligase Chain Reaction (LCR) employing at least one pair of primers. At least a first primer of the at least one pair of primers of these reactions bears an affinity ligand, typically biotin, which binds to a signal producing reagent, typically a streptavidin alkaline phosphatase conjugate. In addition, when the capture reagent is an anti-sulfonated DNA antibody at least one second primer of the at least one pair of primer for the enzymatic amplification bears an affinity ligand, typically a sulfonated cytosine, which is bound by the capture reagent of the capture zone 32. After a number of amplification cycles, typically between 1 and 50 cycles, an aliquot of a reaction mixture is assayed using apparatus 10.

When the capture reagent is an anti-sulfonated DNA antibody, an aliquot of the reaction mixture containing target nucleic acid sequences, oligonucleotide primers, and nucleotides, typically between 1 and 20 μl is added to well 14. Approximately 30 μl of a solution containing a signal producing reagent, typically streptavidin alkaline phosphatase conjugate in a TPG running buffer (0.3% Tween 20 and 1% gelatin in PBS), is also added to well 14 and the contact portion 20 of strip 22 is placed in well 14 in contact with the reaction mixture. The reaction mixture containing the target molecules including the nucleic acid sequences is carried through the bibulous carrier 24 by capillary transport, past the capture zone 32 where the target molecules are captured by the capture reagent, to the absorbent pad 27.

After about 10 minutes most of the molecules that include labeled nucleic acid sequences (typically more than 80% of the labeled molecules) are captured in the capture zone 32. The contact portion 20 of the strip 22 is then removed from the well 14 and placed in the well 16.

The well 16 typically contains about 50 μl of TP buffer (0.3% tween in PBS) which is carried through the bibulous carrier 24 to the capture zone to remove non-specifically captured compounds which may interfere with the detection of the target nucleic acid sequence. After about 10 minutes strip 22 is removed from well 16 and immersed in well 18.

Well 18 contains about 300 μl of signal developing reagent solution, typically a Chemiprobe™ solution containing the chromogenic substrate, BCIP/NBT, commercially available from Orgenics Ltd., Yavne Israel). This solution covers the capture zone 32. The signal producing reagent, alkaline phosphatase, which is attached to the labeled molecules in the capture zone 32 then converts the chromogenic substrate to a precipitable color which is a sensible signal indicating detection of the target nucleic acid sequences.

When the capture reagent is a nucleic acid complementary to at least part of the target nucleic acid sequence an aliquot of the reaction mixture is typically diluted with a hybridization solution typically composed of 0.6M NaCl, 20 mM phosphate buffer, pH 7.5, 0.02% Ficoll 400 (Sigma, St. Louis, Mo., USA), 0.02% gelatin and 1% PVP. The sample is then typically boiled and chilled immediately and an aliquot of each solution transferred to the wells 14 of the apparatus 12. The contact portion 20 of each strip 22 is then typically brought into contact with the solution in the wells 14.

Apparatus 10 is then typically placed in a humid incubator for approximately 25 minutes and the solution allowed to migrate through the nitrocellulose strips forming the bibulous carrier 24. The solution containing the target molecules including the nucleic acid sequences is carried through the bibulous carrier 24 by capillary transport to the absorbent pad 27 and past the capture zone 32 where the target molecules are captured by the nucleic acid complementary to the target nucleic acid sequence.

The strips 22 are then typically transferred to wells 16 containing streptavidin alkaline phosphatase conjugate. The strips 22 are then typically transferred to wells 18 containing a solution including 150 μ of 0.3% Tween 20 in PBS and the contact portion 20 of the strip 22 was brought into contact with the solution for approximately 15 minutes.

Finally the strips 22 are then typically completely immersed in a ChemiProbe™ BCIP/NBT solution in a set of wells not shown in the figures for approximately 20 minutes to provide a substrate for a chromogenic reaction. A blue colored signal in the capture zone 32 of strip 22 indicating the presence the target molecules.

Figure 1:
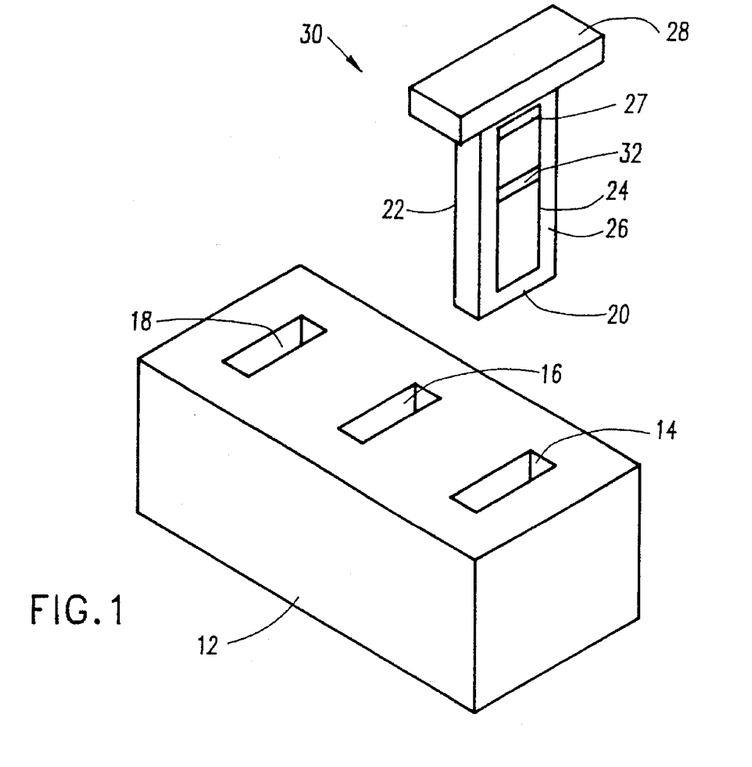
FIG. 1 is a front view pictorial illustration of apparatus for separation of a target nucleic acid sequences from non-target nucleotides and oligonucleotides in a liquid sample, concentration of the target nucleic acid sequences, and detection of the concentrated target nucleic acid sequences constructed and operative in accordance with the present invention and shown before use.
Figure 2:
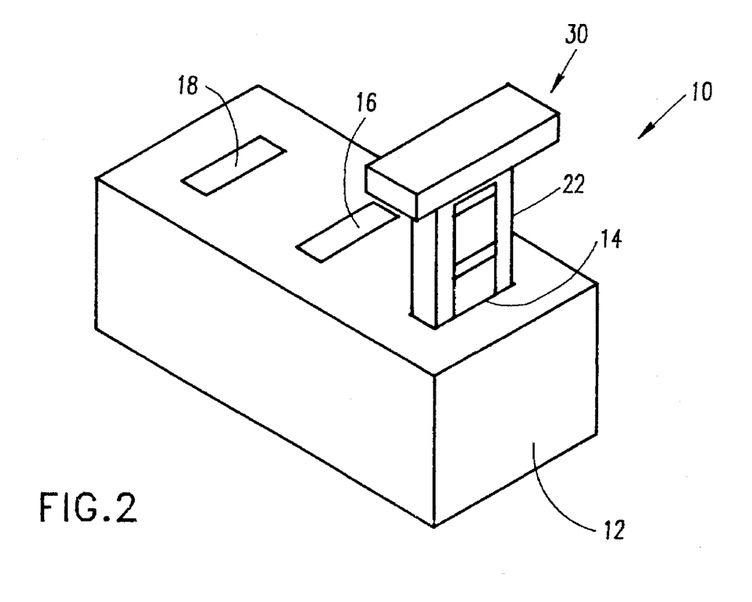
FIG. 2 is a front view pictorial illustration of the apparatus of FIG. 1 shown during use.
Figure 3:
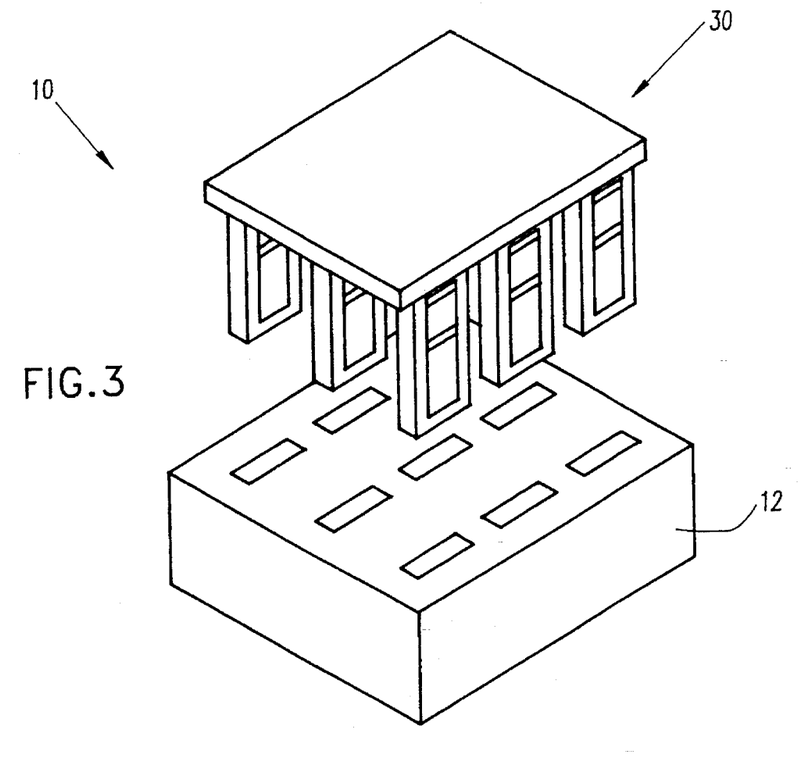
FIG. 3 is a front pictorial view of an alternative embodiment of the apparatus of FIG. 1 shown before use.
Figure 4:
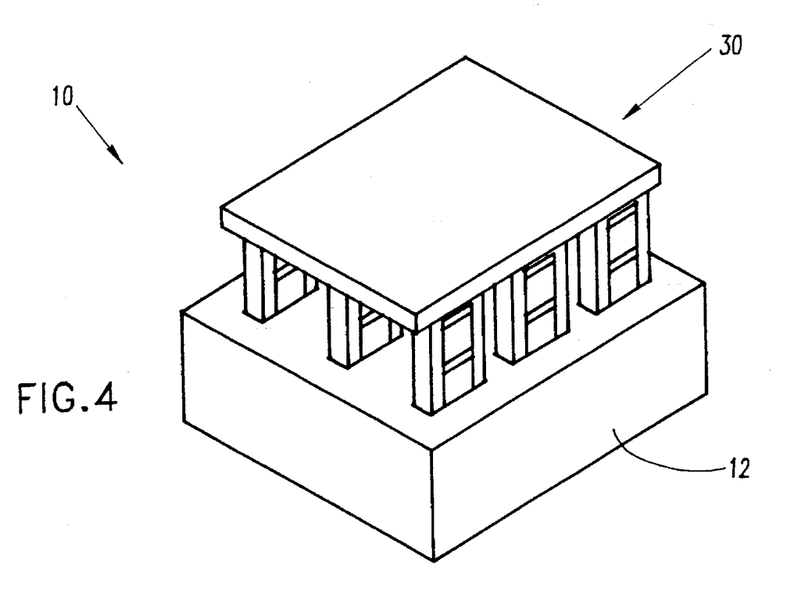
FIG. 4 is a front pictorial view illustration of the apparatus of FIG. 3 shown during use.

As can be seen in FIGS. 3 and 4 more then one strip 22 can be attached to handle 28 to permit more that one assay to carried out at the same time.

Reference is now be made to the following examples which, together with FIGS. 1–4 illustrate the invention.

EXAMPLE 1

TRANSPORT AND CONCENTRATION OF DNA ON NITROCELLULOSE a) Sequence synthesis and labeling of primers Primers were selected in the gene of HIV-1 and had the following sequences:

Primer 3 (SEQ ID NO: 1)
5'TGGGAAGTTCAATTAGGAATACCAC
Primer 3 (SEQ ID NO: 2)
5'TGGGAAGTTCAATTAGGAATA
Primer 4 (SEQ ID NO: 3)
5'CCTACATACAAATCATCCATGTATTC The primers were synthesized on Applied Biosystems 380A DNA Synthesizer (Applied Biosystems, Hayward, Calif., USA) and purified using OPC rapid purification cartridges (Applied Biosystems, Calif., USA).

Primer sulfonation

The primer 3'(SEQ ID NO: 2) was synthesized with a 13 mere Polycytosine Tail at the 5' end. These primer was then sulfonated according to the protocol described in the ChemiProbe™ kit (commercially available from Orgenics Ltd.).

100 μl of C Tail primer (0.5 mg/ml) was mixed with 50 μl of solution A of the ChemiProbe™Kit (4 M sodium bisulfite) and 12.5 μl of solution B of the ChemiProbe™ Kit (1M methoxyamine) and incubated overnight at 20° C. Sulfonated oligonucleotides were then desalted by centrifuging through a 2 ml bed of Sephadex G-50 spin column.

Primer biotinylation

Primer 4'(SEQ ID NO: 3) was synthesized in the 5' end with a 12 mere polycytosine in which 4 cytosine nucleotides were replaced by $N^4$-LCA-5-methyldeoxycytidine (American Bionetics, Hayward, Calif., USA) as follows CCCCCCCCCCCC, where C indicates the modified cytosine. These oligonucleotides were purified by acrylamide gel according to the procedures described by Maniatis, T. et al., Molecular cloning: a laboratory manual, 1989, p 646, Cold Spring Harbor Laboratory, Cold Spring Harbor, N.Y. the teachings of which are herein incorporated by reference.

The purified oligonucleotides were then biotinylated according to the following procedure:

10 mole of desiccated primers were dissolved in 50 μl of 100 mM Borate Buffer and added to 50 μl of dimethyl formamide (DMF) containing 0.1 mg of biotin N Hydroxy succinimide (Pierce, Rockford, Ill. USA). This solution was then incubated overnight at 20° C. and then purified through a Nensorb 20 column (Du Pont Company, Wilmington, Del., USA) according to the instructions of the supplier. The primers were then concentrated by evaporation and resuspended with water to the original concentration.

b) Amplification of the HIV sequence

100 μl of a mixture containing 1 μg of extracted DNA from a positive HIV sample (extraction procedure according to Edwards et al., The Journal of Pediatrics, 1989, vol. 45, pp 200–203) the teachings of which are herein incorporated by reference. 100 pmole of each primer P3 and P4, 0.25 mM of the four deoxynucleotide triphosphate (dNTP), 10 μl 10X Taq Buffer (Promega, Madison, Wis. USA) and 2.5 U of Taq polymerase (Promega) was amplified under the following conditions on a programmable Grant (Cambridge, U.K.) water bath.

A first DNA denaturing step of 5 minutes at 94° C. was followed by 30 cycles of 1 minute denaturing at 94° C. 1 minute DNA annealing at 52° C. and 1 minute DNA elongation at 72° C. The amplification was ended with a seven minute elongation step at 72° C.

A second amplification was performed for 20 cycles under the same conditions as the first amplification but using the labeled biotinylated and sulfonated primers described above. The DNA template employed was 1 μl of the first PCR mixture diluted in 100 μl of a mixture containing 100 pmoles of each labeled primer, 0.25 mM of the four deoxynucleotide triphosphate, 10 μl of 10X Taq buffer (Promega) and 2.5 U of Taq polymerase (Promega). Primers were excluded from the PCR Product by mixing 100 μl of the reaction mixture with 60 μl of polyethylene glycol (PEG) 4000(Sigma, St. Louis. Mo., USA) in 2.5 M NaCl solution. This mixture was then incubated for one hour at 4° C. Then, after 10 minutes of centrifugation at 10,000× g at 4° C. the supernatant was discarded and the pellet was resuspended in 100 μl of water.

c) Preparation of nitrocellulose backed strips

1. Mylered Nitrocellulose (pore size 3 μ) (Schleicher & Schuell, Dussel, Germany) were cut into lengths of 0.5×3.0 cm to form the bibulous carrier 24 of the apparatus of FIGS. 1–4. The bibulous carriers 24 formed strips 22. One microliter of purified mouse monoclonal anti-modified DNA (2 mg/ml), commercially available from Orgenics Ltd., catalog no. 10793010, supplemented with 1% sucrose in phosphate buffered saline (PBS) was embedded in the middle of the nitrocellulose strips in a horizontal line to form the capture zone 32. The strips were then air dried for 1 hour at 37° C.

Free absorption sites were then blocked by incubating the strips for 2 hours in a solution of 1% gelatin (Norland Products Inc., New Brunswick Canada), and 0.05% Tween 20 (Sigma) in PBS. The nitrocellulose strips were then briefly washed in water, dried for one hour in an incubator at 37° C. and stored under desiccation for at least four months. A square of 0.5×2 cm of Whatman 3MM paper was attached to the top of the strip to serve as an absorbent pad 27.

2. Mylered nitrocellulose lengths were prepared as above but without the blocking step.

d) Transport and concentration of the DNA

The PCR reaction mixture was diluted ten fold in either TGP running buffer (0.30% Tween 20 and 1% gelatin in PBS), or PBS. 30 μl of each solution were then transferred to wells similar to the wells of apparatus 12 shown in FIGS. 1–4 and the contact portion 20 of each strip 22 was brought into contact with the solutions.

The solution was allowed to migrate through the nitrocellulose strips forming the bibulous carrier 24 at room temperature for 10 minutes. The strips 22 were then covered completely by a solution of streptavidin alkaline phosphatase conjugate (Enzymatix, Cambridge, U.K.) diluted 1:2,500. After a 10 minute incubation at room temperature the strips were washed briefly with water and then covered by BCIP/NBT ChemiProbe™ solution (Orgenics Ltd.). After 5 minutes the strips were briefly washed with water and inspected. The color was then stabilized by a brief washing in ethanol and then dried at room temperature. A strip 22 was considered positive for HIV if a purple line appeared in the capture zone.

Running the HIV product of PCR amplification on nitrocellulose strips using PBS as a buffer wherein the absorption sites of the nitrocellulose strips were not blocked failed to produce a positive reaction. The strips 22, however, in which the free absorption sites of the nitrocellulose were blocked by gelatin solution produced a visible signal when PBS was used as a running buffer. In addition, the strips 22, wherein the absorption sites were not blocked prior to their contact with PCR reaction mixture solutions produced a visible signal when the TGP running buffer was used. The strongest signal was obtained when both a blocked strip and the TGP running buffer were used.

These results indicate that amplified nucleic acid sequences can migrate by capillary movement through nitrocellulose strips wherein the absorption sites of the nitrocellulose are blocked either prior to or during the capillary transport of the nucleic acid sequences. Moreover these results also indicate that amplified DNA in a solution may be concentrated by contacting blocked nitrocellulose strips at a contact point with a solution containing amplified DNA and capturing the amplified DNA at an appropriate capture site on the nitrocellulose strip downstream of the contact point.

EXAMPLE 2

TRANSPORT AND CONCENTRATION OF GENOMIC AND PLASMID DNA ON NITROCELLULOSE

Human Placenta DNA (Sigma), CasKi cells DNA and Bluescript plasmid DNA were prepared and sulfonated as described by Nur et al. (Ann. Biol. Clin., 1989, 47, 601–606) with each molecule of CasKi cell DNA or Human Placental DNA having about $10^{15}$ base pairs. HIV specific PCR products were amplified with one primer being sulfonated another primer being biotinylated, thus double labeling the PCR products as described in Example 1. The nitrocellulose strips 22 having blocked absorption sites were also prepared as described in Example 1.

One μl of a 20 μg/ml solution of each of the three types of DNA (either sulfonated or unsulfonated) was added to 20 μl of TGP running buffer. The DNA solution was loaded into wells and the contact portion 20 of the strips 22 brought into contact with this solution. After 10 minutes the strips were removed from the DNA solution and transferred to other wells where the contact portion 20 of the strips 22 was brought into contact with double label PCR product (diluted 1:20 from the HIV PCR reaction mixture solution of Example 1) and streptavidin alkaline phosphatase conjugate (Enzymatix, Cambridge, U.K.) diluted 1:2,500 in TGP running buffer. After 10 minutes of contact with the double label DNA product the strips 22 were washed for 10 minutes by contacting the contact portion of strips 22 with a washing solution of TGP buffer. Finally, the strips 22 were immersed in a ChemiProbe™ BCIP/NBT solution (commercially available from Orgenics Ltd.) for a 5 minute incubation period as described in Example 1.

It was found that all three types of DNA, Placental DNA, CasKi cell DNA and Bluescript plasmid DNA, when sulfonated completely prevent the development of a visible signal in the capture zone 32. In contrast to these results, solutions containing the same DNA, but where the DNA was not sulfonated failed to inhibit the signal. These results indicate that both genomic DNA and plasmid DNA can be transported by capillary movement of a liquid through a nitrocellulose carrier and that this DNA can be concentrated at an appropriate capture site on the nitrocellulose strip.

The above results also suggest that the presence of target DNA in a sample can be detected by the reduction in signal produced by the double label PCR product when target DNA is sulfonated and bound to the capture zone 32 before capturing the double label DNA as described above.

EXAMPLE 3

COMPARISON OF DETECTION SYSTEMS

Primers were selected in the E6 gene of the HPV genome and were consensus primers for HPV 16, HPV 18 and HPV 33 described in Israel Patent Application No. 097226 the teachings of which are herein incorporated by reference. These primers had the following sequences:

| Primer h1 (SEQ ID NO: 4) 5'AAGGGAGTAACCGAAATCGGT | Primer h2 (SEQ ID NO: 5) 5'ATAATGTCTATATTCACTAATT |
|---|---|

The primer synthesis and labeling procedure was described in Example 1. Primer h1(SEQ ID No: 4) was sulfonated and Primer h2(SEQ ID NO: 5) biotinylated according to these procedures.

Amplification and labeling of HPV DNA SEQUENCE

100 μl of reaction mixture containing 100 pmole of labeled or unlabeled primers, 1 μg of DNA extracted from cervical biopsies according to the instructions of the Hybri-Comb™ HPV kit (commercially available from Orgenics Ltd.), 0.25 mM of deoxynucleotide triphosphate (dNTP), 10 μl 10X Taq buffer (commercially available from Promega), and 2.5 units of Taq polymerase (commercially available from Promega). The thermocycling of the mixture was performed with a Grant programmable water bath.

A first PCR step was performed using the unlabeled primers. Each amplification cycle consisted of: DNA denaturing for 1 minute at 94° C., annealing step 1 minute at 55° C., and DNA extension step for 1 minute at 72° C. The amplification reaction was terminated by 5 minutes of extension at 72° C. after 20 cycles. A second PCR step using labeled primers was performed according to the following procedure. One μl of the first reaction mixture was added to each of six replicates containing 100 μl of reaction mixture identical to that of the first PCR reaction (except that labeled rather than non-label primers were used). Each replicate was amplified for either 0, 10, 20, 25, or 30 cycles and then stored at 4° C.

Detection of the PCR product

1. Detection by ethidium bromide—EtdBr.

After amplification, 10 μl of the PCR mixture was electrophoresed on 8% non-denaturing (TAE) Tris-acetic acid buffer polyacrylamide gel and electrophoresed for 1 hour at 50 mA. Gels were submerged for 15 min. in 10 μg/l of ethidium bromide (EtdBr) and DNA was visualized by UV light.

2. Detection by Southern blot.

After separation by electrophoresis the migrated PCR fragments were electroblotted onto Hybond-N membrane (commercially available from Amersham, Bucks, U.K.) using TAE buffer as the transfer buffer in a Trans Blot Cell (Commercially available from Bio-Rad, Richmond, Calif., USA) for 3 hours at 1.5 Amp. The membrane was then air dried and baked for 2 hours at 80° C.

Visualization of the biotinylated label was performed as follows: The membrane was blocked by PBS supplemented with 1light (Tropix, Mass., USA) and 0.1% Tween 20. The nylon membrane was incubated for 1 hour in the same blocker supplemented with streptavidin alkaline phosphatase conjugate diluted 1:2500 and then washed by a solution containing 0.1% Tween 20 in PBS. Finally, the membrane immersed in a ChemiProbe™ BCIP/NBT chromogenic solution for 30 minutes and the excess chromogen rinsed with water.

3. Detection by solid support capture (dip-stick) assay.

Non—bibulous impact polystyrene (commercially available from Orgenics Ltd.) was used as a solid support for a dip-stick type capture assay.

Preparation of the dip-stick.

One microliter of a solution of 2 mg/ml purified mouse monoclonal anti-modified DNA in PBS was applied to the lower portion of the dip-stick and then dried for 1 hour at 37° C. The unbound sites were blocked by dipping the dip-stick into a solution of 1% gelatin and 0.05% Tween 20 for 1hour. The dip-sticks were then washed for 2–5 seconds in water and dried at 37° C. for 1 hour. The assay:

5 μl of a reaction mixture solution from each of the second PCR cycle groups was added to 45 μl of TGP running buffer containing streptavidin alkaline phosphatase conjugate (1:200). The solutions were placed in wells and the dip-stick was dipped into the solutions. After 30 minutes incubation the dip-sticks were washed in PBS and dipped in BCIP/NBT solution for 20 minutes. The reaction was terminated by washing the dip-sticks in water.

4. Detection by Capillary DNA Concentration Assay (CDCA).

3 μl of each of reaction mixture solution from each of the second PCR cycle groups was added to wells containing 30 μl of solution containing streptavidin alkaline phosphatase conjugate diluted 1:2,500 in TGP running buffer. Nitrocellulose strips were prepared as in Example 1. The contact portion 20 of the strips 22 were brought into contact with the solution in the wells for 10 minutes. The contact portion of the strips 22 were then brought into contact for 10 minutes with wells containing 50 μl of washing solution (TP buffer). Finally, the strips 22 were completely immersed in a ChemiProbe™ BCIP/NBT solution for 5 minutes to provide a substrate for a chromogenic reaction.

The results of the above procedures are present in Table 1 which indicates the detection limit in relation to the number of PCR cycles for the assays described above—EtdBr, Southern blot, solid support capture assay and CDCA.

TABLE 1

Detection Limit of Several Systems

| System | \# of PCR cycles | | | | | |
|---|---|---|---|---|---|---|
| | 0 | 10 | 15 | 20 | 25 | 30 |
| Etd/br | − | − | ± | + | + | + |
| Southern blot | − | ± | + | + | + | + |
| dip-stick | − | − | ± | + | + | + |
| CDCA | − | + | + | + | + | + |

± = threshold levels
− = definite negative
+ = definite positive

As can be seen from Table 1 the sensitivity of the dip-stick test is similar to that of the EtdBr fluorescence test, both of which are less sensitive than the Southern Blot technique. The CDCA was seen to be at least as sensitive as the Southern blot technique.

EXAMPLE 4

EFFECT OF PRIMER ELIMINATION AFTER AMPLIFICATION ON THE SENSITIVITY OF THE CDCA PROCEDURE

Specific HIV sequences were amplified from a positive HIV sample in a 100 μl reaction mixture for 20 PCR cycles using 100 pmole of unlabeled Primer 3' and Primer 4' as described in Example 1. The second amplification was performed under the same conditions as the first amplification but with labeled primers and for 2, 4, 6, 8, 10, and 20 cycles. The template for the second PCR amplification was 1 μl of the first PCR mixture diluted in 100 μl of reaction mixture containing 100 pmoles of each labeled primer, 0.25 mM of the four deoxynucleotide tryphosphate, 10 μl of 10X Taq buffer (Promega) and 2.5 U of Taq polymerase (Promega). For each PCR amplification cycle number group, 4 aliquots of 100 μl of PCR reaction mixture were tested, one for each assay.

Assay-1.

The first assay was the CDCA system described in Example 3. From each PCR amplification cycle number group, 3 μl of reaction mixture were added to wells containing 30 μl streptavidin alkaline phosphatase in TGP running buffer and the CDCA was performed as described in Example 3.

Assay-2

In the second assay the PCR reaction mixture was treated with PEG to remove primers before running the CDCA Primers of each PCR amplification cycle number group were excluded using a PEG solution as described in Example 1. 3 μl of the PEG treated PCR amplification mixture was added to 30 μl of TGP running buffer and the assay then performed as in Example 3.

Assay-3

In the third assay primers in the PCR reaction mixture were excluded by Sephadex G-100 prior to CDCA. Primers of each of the PCR amplification cycle number group were excluded by Sephadex G-100 as follows. 0.5 ml of Tris EDTA buffer (TE) in Sephadex G-100 (Pharmacia) was transferred to a well, excess TE was absorbed by filter paper. 15 μl of each PCR reaction mixture solution was diluted 1:1 with TGP running buffer and the mixture placed directly in the bottom of the well.

The contact portion 20 of a strip 22, including a strip of nitrocellulose wherein the absorption sites are blocked was prepared as in Example 1, was brought into contact with the upper side of the Sephadex G-100 for 25 minutes. The contact portion of the strip 22 was then brought into contact for 10 minutes with streptavidin alkaline phosphates conjugate diluted 1:2,500 in TGP running buffer in a well, then washed and visualized according to the procedure of Example 1.

Assay-4

In the fourth assay primers were removed from the PCR reaction mixture prior to the CDCA by hybridization of the primers to complementary oligonucleotide sequences bound to a compound. Primers of each PCR amplification cycle number group were trapped by being brought into contact with beads coated with oligonucleotides having sequences complementary to the sequences of the primers to be trapped.

a) Preparation of the trapping system. Streptavidin was bound to styrene/vinyl carboxylic acid beads (5 μm in diameter commercially available from Bangs Laboratories, Inc. Carmel, Ill., USA) according to the principles of Woodward, R. B. and Elofson, R. A. (1961). J. Amer. Chem. Soc. 83, 1007–1010 under conditions described in Israel Patent Application 098452, the teachings of which are herein incorporated by reference. The complementary oligonucleotide sequence, 5' TATTCCTAATTGAACTTCAA (SEQ ID NO: 6). A was synthesized and biotinylated as described in Example 1.

The oligonucleotide was bound to the beads by the following procedure. 100 μl of 1% coated beads were mixed 1:1 with a solution of 1 mg/ml of biotinylated oligonucleotide. The solution was incubated for 3 hours at 30° C. The unbound oligonucleotide was washed in PBS and kept in a solution of 1% gelatin in PBS.

b) The assay procedure

3 μl of each PCR amplification cycle number group was added to wells containing 30 μl of a solution containing 0.50% complementary oligonucleotide coated beads and streptavidin alkaline phosphatase conjugate (diluted 1:500) in TGP buffer and allowed to incubate for 10 minutes.

A contact portion 20 of strip 22, including a nitrocellulose strip wherein the absorbent sites were blocked and was prepared as in Example 1, is then brought into contact with the incubated solution for 10 minutes. The strip 22 was then washed and the signal developed as in Example 3.

Table 2 shows the effect of elimination of primers after amplification on the sensitivity of the CDCA.

TABLE 2

Detection Limit of Assays 1–4

| System | Number of PCR cycles | | | | | |
|---|---|---|---|---|---|---|
| | 0 | 2 | 4 | 6 | 8 | 10 | 20 |
| Assay 1 | | | | | | + | + |
| Assay 2 | | + | + | + | + | + | + |
| Assay 3 | | | + | + | + | + | + |
| Assay 4 | | | | + | + | + | + |

+ = detection of the HIV DNA sequences.

As can be seen from Table 2 untreated PCR solution fails to provide a visible signal in the CDCA assay even after 8 cycles of amplification. Only after some 10 cycles does a positive response appear. Elimination of the primers after amplification by a separation stage or during the test enables the detection of target nucleic acid sequences after only 2–6 PCR cycles. Elimination of primers by each technique has been confirmed by gel electrophoresis and visualization by EtdBr (data not shown).

EXAMPLE 5

DETECTION OF HPV SEQUENCES IN CLINICAL SAMPLES BY HYBRIDIZATION IN SOLUTION

Preparation of the probe.

A single stranded HPV sequence was prepared by asymmetric PCR amplification using the HPV primer h1 described in Example 3. The following conditions for amplification were employed. 10 ng of non-labeled HPV PCR product prepared as described in example 3 was used as a template and only one primer h1 was used for amplification. 50 PCR cycles were performed as described in Example 3.

The single stranded product was then sulfonated for one hour at 30° C. and was then desalted by using Sephadex G-50 as described in the instructions for the use of the Chemiprobe™ kit (Orgenics, Ltd.)

Amplification of the HPV Sequence

The HPV sequences were amplified from a clinical sample by two methods: A) using biotinylated h2 primers and non labeled h1 primers and B) using biotinylated h2 primers and sulfonated h1 primers. For both methods PCR was performed as described in Example 3 for 35 cycles.

Hybridization

5 μl of the PCR reaction mixture solution of method A (after 35 cycles) was added to 95 82 1 of a hybridization solution containing 0.66M NaCl, 65mM sodium citrate, 0.3 mM EDTA, 0.1 M phosphate buffer pH 6.6, 0.02% Ficoll™, 0.2% Polyvinylpyrolidone, 0.5% Polyethylglycol, 0.12% bovine serum albumin, and 100 ng of a sulfonated probe described above. The solution was then heated for 5 minutes at 95° C. and cooled immediately. Hybridization was performed for 45 minutes at 65° C.

Capture by CDCA

3 μl of the hybridization mixture after completion of the hybridization or 0.3 μl of PCR reaction mixture solution from method B were added to wells containing 30 μl of streptavidin alkaline phosphatase in TGP running buffer. A contact portion 20 of strip 22, including a nitrocellulose strip which was prepared as in Example 1, was then brought into contact for 10 minutes with the solution in the well, the hybrid was captured and visualized as in Example 3.

Results

Twelve samples were evaluated. The same 5 samples were found positive and the same 7 samples found negative for both methods tested.

EXAMPLE 6

DETECTION OF HPV IN THE CDCA. SYSTEM USING COLORED LATEX BEADS AS THE COLOR GENERATING REAGENT

Streptavidin (Sigma) was covalently bound to 0.2 μm styrene/vinyl carboxylic acid colored beads (Bangs Laboratories Inc., Carmel, Ill., USA). The binding was accomplished by the methods of Woodward et al. as described in Example 4.

PCR product from a clinical sample suspected to contain HPV sequences were amplified by a second PCR amplification step using h-1 sulfonated and h-2 biotinylated primers as described in Example 3. Primers were excluded from the PCR reaction mixture solution using PEG solution as described in Example 1. 3 μl of this solution was added to a well containing 0.05% of streptavidin bound beads in 1.0% gelatin, 0.3% Tween 20 and 0.25 M NaCl. The contact portion 20 of a strip 22 prepared as described in Example 3 was placed in the well, in contact with the solution in the well. After a few minutes a blue colored signal was visible in the capture zone 32 of the strip 22.

EXAMPLE 7

DETECTION OF HPV SEQUENCES IN A CAPILLARY DNA CONCENTRATION ASSAY USING DNA AS A CAPTURE REAGENT a) Selection of primer Primers were selected in the E6 gene of HPV/16 and had the following sequences:

| Primer 1 (SEQ ID NO: 7) |
| 5'AAGGGCGTAACCGAAATCGGT |
| Primer 2 (SEQ ID NO: 8) |
| 5'GTTGTTTGCAGCTCTGTGC | b) Oligonucleotide probe capture reagent

The oligonucleotide probe which serves as a capture reagent was selected to be complementary to the sequence of a biotinylated strand produced by the elongation of primer 2' in a PCR reaction. The following sequence was chosen (SEQ ID NO: 9): CAACAACAACAAGTTTCAGGACCCACAGGAGCGACCC c) preparation of the Nitrocellulose backed strips Mylered nitrocellulose, pore size 5 microns, (Micron Seperation Inc., Westboro, Mass., USA) was cut into 0.5× 3.0 cm strips. One microliter of a solution composed of 5 ng oligonucleotide probe capture reagent in 10× SSC (SSC consisting of 0.15M NaCl and 0.015M sodium citrate, pH 7.0) was applied to middle of each nitrocellulose strip forming a spot. The strips were then dried for 15 minutes at 37° C. and the oligonucleotide probes were then fixed to the nitrocellulose strips by exposure of the strips to UV radiation for 5 minutes.

d) Amplification of the HPV sequence

PCR amplification was performed in a reaction mixture of 100 μl aliquots containing either 1,000, 100, 10, 1 or 0 pg of CasKi cell DNA in the presence of 1 μg normal human placenta DNA. Each PCR reaction mix additionally contained 100 pmole of each of the primers (P1 and P2), 0.25 mM of the four deoxynucleotide triphosphates, 10 μl 10X Taq buffer and 2.5 U of Taq DNA polymerase.

A first DNA denaturing step of 5 minutes at 94° C. was followed by 30 cycles of 1 minute denaturing at 94° C., 1.5 minute annealing at 47° C. and 1.5 minute elongation at 72° C. The amplification was ended with a seven minute elongation at 72° C.

e) Transport and concentration of DNA

The concentration and capturing of target nucleic acid sequences was achieved by the following chromatography hybridization procedure:

50 μl of each PCR product obtained in step d above was diluted 1:10 in 450 μl of hybridization solution composed of 0.6 M NaCl, 20 mM phosphate buffer, pH 7.5, 0.02% Ficoll 400(Sigma, St. Louis, Mo., USA), 0.02% gelatin and 1% PVP. The samples were boiled for 10 minutes and chilled immediately on ice. 200 μl of each solution was then transferred to the wells 14 of the apparatus 12 shown in FIGS. 1–4 and the contact portion 20 of each strip 22 was brought into contact with the solution in the wells 14.

The apparatus 12 was placed in a humid incubator (90% relative humidity) at 37° C. for 25 minutes and the solution was allowed to migrate through the nitrocellulose strips forming the bibulous carrier 24. The strips 22 were then transferred to wells 16 containing 100 μl of streptavidin alkaline phosphatase conjugate diluted 1:2,500 in PBS and 0.3% Tween 20 for 20 minutes. The strips 22 were then transferred to wells containing a solution including 150 μl PBS and 0.3% Tween 20. The contact portion 20 of the strip 22 was brought into contact with the solution for 15 minutes at 37° C. Finally the strips 22 were completely immersed in a ChemiProbe™ BCIP/NBT solution for 20 minutes at 37° C. to provide a substrate for a chromogenic reaction. A blue colored signal in the capture zone 32 of strip 22 indicating the presence of HPV DNA.

It was found that HPV sequences existing in as low as 1 pg CasKi DNA can be detected by this chromatography hybridization procedure.

It will be appreciated by persons skilled in the art that the present invention is not limited to what has been particularly shown and described herein above. Rather the scope of the present invention is defined only by the claims which follow:

---

We claim:

1. A method for transport of nucleic acids in an unblocked bibulous carrier comprising:

providing a dry unblocked bibulous carrier defining a capillary transport path which supports the transport of nucleic acids; and contacting the dry unblocked bibulous carrier with a solution comprising nucleic acids and at least one blocking agent comprising an nonionic detergent allowing nucleic acids to transport along said carrier by capillary transport.

2. Apparatus for transport of nucleic acids in an unblocked bibulous carrier, the apparatus comprising:

a dry unblocked bibulous carrier defining a capillary transport path which supports the transport of nucleic acids; and a solution comprising nucleic acids and at least one blocking agent comprising an nonionic detergent, said solution contacting the dry unblocked bibulous carrier.

3. A method according to claim 1 wherein said nucleic acids comprise at least an amplified portion of a target nucleic acid.

4. A method according to claim 1 further comprising capturing at least some of the nucleic acids with at least one capture reagent immobilized in at least one capture zone on the dry unblocked bibulous carrier downstream of a portion of the dry unblocked bibulous carrier contacting the solution.

5. A method according to claim 1 further comprising capturing at least some of the nucleic acids by hybridization with at least one nucleic acid capture reagent immobilized in at least one capture zone on the dry unblocked bibulous carrier downstream of a portion of the carrier contacting the solution.

6. A method according to claim 1 further comprising amplifying, by an enzymatic reaction, at least a portion of a target nucleic acid to produce copies of said nucleic acid, and providing said copies in said solution.

7. A method according to claim 1 wherein said nucleic acids are produced by a method which incorporates at least one pair of oligonucleotide primers into said nucleic acids.

* * * * *